(12) United States Patent
Imai et al.

(10) Patent No.: US 6,566,418 B2
(45) Date of Patent: May 20, 2003

(54) CALCIUM HYDROXIDE-BASED ROOT CANAL FILLING MATERIAL

(75) Inventors: Yohji Imai, Chiba (JP); Masao Abiru, Tokyo (JP)

(73) Assignee: GC Corporation, Tokyo (JP)

( * ) Notice: Subject to any disclaimer, the term of this patent is extended or adjusted under 35 U.S.C. 154(b) by 8 days.

(21) Appl. No.: 09/768,285

(22) Filed: Jan. 25, 2001

(65) Prior Publication Data

US 2002/0198283 A1 Dec. 26, 2002

(30) Foreign Application Priority Data

Feb. 4, 2000  (JP) ........................................ 2000-027776

(51) Int. Cl.⁷ .......................... A61K 6/083; A61C 5/00; C08K 3/22
(52) U.S. Cl. ....................... 523/116; 523/117; 523/118; 524/401; 433/224; 433/226
(58) Field of Search ................................ 523/116, 117, 523/118; 433/199.1, 201.1, 224, 226; 524/401

(56) References Cited

U.S. PATENT DOCUMENTS 4,647,600 A * 3/1987 Kawahara et al.
5,455,024 A * 10/1995 Winston et al. ................ 424/52
5,934,460 A * 8/1999 Schmid ........................ 206/210
6,197,846 B1 * 3/2001 Combe et al. ............... 523/116

* cited by examiner

Primary Examiner—Tae H. Yoon
(74) Attorney, Agent, or Firm—Oblon, Spivak, McClelland, Maier & Neustadt, P.C.

(57) ABSTRACT

A calcium hydroxide-based root canal filling material having superior bioaffinity is provided, which is a temporary root canal filling material to be used in the root canal treatment of teeth, having such roles that, when filled temporarily in the root canal, it stays in an affected part during a predetermined period of time, thereby a root canal being prevented from staining by pathogenic bacteria or exudates, has corrosion resistance, and promotes the remedy of an apical abscess by wound of the root apex portion. The calcium hydroxide-based root canal filling material is comprised of 3 to 20% by weight of polyvinylpyrrolidone and/or polyvinyl methyl ether, 30 to 60% by weight of calcium hydroxide, and 35 to 60% by weight of water. Further, there is an embodiment in which from 5 to 20 parts by weight of at least one X-ray opacity medium selected from barium sulfate, zirconium oxide, bismuth subnitrate, bismuth trioxide, and bismuth carbonate and/or 0.5 to 5 parts by weight of at least one disinfectant selected from iodoform and iodine is further contained based on 100 parts by weight of the calcium hydroxide-based root canal filling material.

6 Claims, No Drawings

CALCIUM HYDROXIDE-BASED ROOT CANAL FILLING MATERIAL

BACKGROUND OF THE INVENTION

1. Field of the Invention

The present invention relates to a calcium hydroxide-based root canal filling material, which is a temporary root canal filling material that is used for a short period of time after root canal preparation, in the root canal treatment of teeth, a pulp tissue is removed with an instrument for root canal preparation such as a reamer or a file, thereby a root canal being prepared into a form in which the root canal filling can be readily achieved, but before a final root canal filling material such as a gutta-percha is filled into the prepared root canal. This calcium hydroxide-based root canal filling material has such roles that, when filled temporarily in the root canal, it stays in an affected part during a predetermined period of time, thereby preventing the root canal from staining by pathogenic bacteria or exudates, has corrosion resistance, and promotes the remedy of an apical abscess by wound of the root apex portion.

2. Background of the Invention

In the dental remedy, there is taken a treatment that, when the remedy of pulp disease or apical periodontitis of teeth is carried out, sphacelus pieces or food pieces within a root canal and dentins within a stained root canal inner wall are removed, and pulpectomy is then carried out. Simultaneously, there is taken a treatment that the root canal is adjusted into a form in which the root canal filling can be readily achieved with an instrument such as a reamer or a file, and a materially stable substance such as gutta-percha is filled into the prepared root canal, thereby pathogenic bacteria being prevented from invading as well as the tooth root being kept harmless for a periodontal tissue. This treatment in series is called as a root canal remedy.

Now, in order to achieve the root canal treatment, first of all, a dental pulp is removed, and root canal preparation is then performed to enlarge an instrument such as a reamer or a file,. Subsequently, the root canal thus treated is cleaned with a chemical. However, the root canal is complicated, and the number of root canals per tooth is different depending on a site at which the teeth are present, such as a single root canal, two root canals, three root canals, or four root canals. Further, the shape of the root canal varies depending on the individual teeth, including a linear shape, a flat shape, a gutter shape, and a curved shape. For these reasons, even when such a treatment is achieved, there is a fear that bacteria within the root canal and dentinal tubule cannot be removed completely.

Thus, as a treatment for overcoming this fear, a root canal disinfection is taken. As this operation, there is employed a process in which a cotton roll having a chemical (representative examples of the root canal disinfectant include formalin, phenol preparations, and iodine preparations) immersed therein is inserted within a root canal, thereby temporarily the root canal being sealed; the remaining bacteria are disinfected to effect sterilization within the root canal; and disinfection is further effected due to strong alkalinity of calcium hydroxide. After this treatment as root canal disinfection (this treatment is possibly repeated in an interval of about 5 days to one week) has been completed, the root canal is cleaned, the moisture is removed, and a final root canal filling material such as gutta-percha is then filled within the root canal.

This calcium hydroxide has the following characteristics. Rather than a characteristic of its strong transient pharmacological effect, it not only has a soft disinfection effect but also promotes the formation of a tooth tissue so that one can expect biological sealing of an apical foramen, and it is gentle to living bodies. These characteristics are ones not seen in other chemicals. However, to use calcium hydroxide as a disinfectant for root canal is difficult from the standpoint of operability due to its insolubleness in water. In other words, as described above, the root canal is complicated, and the number of root canals per tooth is different depending on a site at which the teeth are present. Accordingly, it is quite difficult to fill the calcium hydroxide within the complicated root canal. Moreover, when the calcium hydroxide does not spread completely into the complicated root canal and even a small gap remains within the root canal, pathogenic bacteria may enter therein also remain. As a result, sealing with the root canal filling material such as gutta-percha is finally carried out in a state that the pathogenic bacteria are present, and a dental prosthesis is set thereon. This possibly causes a worst state where re-remedy must be carried out.

Thus, there is taken a process for filling calcium hydroxide into a root canal by the following means for the purpose of improving the operability. It is a means in which a calcium hydroxide powder is mixed with a mixture of propylene glycol as a tackifier and water. However, in the case where a large amount of the calcium hydroxide powder is contained in the mixture of propylene glycol and water (the large amount of the calcium hydroxide powder as referred to herein means one in which calcium hydroxide sufficiently exhibits a remedy effect by refers to 30 to 60% by weight), the fluidity is lost, leading to a marked reduction in the clinical operability to be of no practical use.

On the other hand, in recent years, a toxicity of propylene glycol to human bodies has been pointed out. Although the calcium hydroxide are characterized to be gentle to living bodies, nevertheless, a serious question in its bioaffinity remains for the use of propylene glycol.

SUMMARY OF THE INVENTION

Thus, the present invention is aimed to provide a calcium hydroxide-based root canal filling material, which is free from propylene glycol as a tackifier and that is superior in bioaffinity and has a proper viscosity.

In order to overcome the above-described problem, we, the present inventors, made extensive and intensive investigations. As a result, it has been found that it is effective to use a predetermined proportion of polyvinylpyrrolidone and/or polyvinyl methyl ether, in order to provide a calcium hydroxide-based root canal filling material, which is free from propylene glycol as a tackifier, is superior in bioaffinity, has a proper viscosity such that it can remain in an affected part during a predetermined period of time, has fluidity suitable for clinical operability, has corrosion resistance while preventing a root canal from staining by pathogenic bacteria or exudates, and promotes the remedy of an apical abscess by wound of a root apex portion, leading to accomplishment of the invention.

Specifically, the calcium hydroxide-based root canal filling material according to the present invention comprises 3 to 20% by weight of polyvinylpyrrolidone and/or polyvinyl methyl ether, 30 to 60% by weight of calcium hydroxide, and 35 to 60% by weight of water.

Also, the present invention includes an embodiment in which from 5 to 20 parts by weight of at least one X-ray opacity medium selected from barium sulfate, zirconium oxide, bismuth subnitrate, bismuth trioxide, and bismuth carbonate is further contained based on 100 parts by weight of the calcium hydroxide-based root canal filling material; an embodiment in which 0.5 to 5 parts by weight of at least one disinfectant selected from iodoform and iodine is further contained based on 100 parts by weight of the calcium hydroxide-based root canal filling material; and an embodiment in which 5 to 20 parts by weight of at least one X-ray opacity medium selected from barium sulfate, zirconium oxide, bismuth subnitrate, bismuth trioxide, and bismuth carbonate and 0.5 to 5 parts by weight of at least one disinfectant selected from iodoform and iodine are further contained based on 100 parts by weight of the calcium hydroxide-based root canal filling material.

DETAILED DESCRIPTION OF THE INVENTION

The details to the development of the present invention as well as the calcium hydroxide-based root canal filling material according to the invention will be hereunder described in detail.

The usefulness of calcium hydroxide as disinfectant for the root canal filling material is widely known. Hitherto, calcium hydroxide and water or physiological sodium chloride were mixed in amounts of approximately 50% by weight, respectively at the time of the use and then provided for the remedy. However, the mixing during the remedy is troublesome, the mixture cannot stay in an affected part during a predetermined period of time because it does not have a viscosity, and its fluidity is not good enough for filling it in the affected part. For these reasons, the development of a premix type preparation having both viscosity and fluidity has been demanded, and those having propylene glycol, water and calcium hydroxide previously mixed with each other are now commercially available. However, in the premix type preparation, calcium hydroxide is contained less than 30% by weight from the standpoint of fluidity. Accordingly, there was involved a problem that it is impossible to contain 30% or more by weight of calcium hydroxide, which is a content to be effective. Thus, the inventors made various investigations with respect to components by which the content of calcium hydroxide can be increased and a proper fluidity can be imparted while a proper viscosity is imparted. As a result, it has been found that polyvinylpyrrolidone and polyvinyl methyl ether are suitable for these purposes.

Polyvinylpyrrolidone has such characteristics that the affinity with living bodies is superior and that the safety is high, as compared with propylene glycol that has hitherto been used as a tackifier, and is a water-soluble polymer used as an additive of medical preparations or for a contact lens. Further, polyvinyl methyl ether is a material generally used as a water-soluble tackifier and the fluidity does not reduce even when the amount of calcium hydroxide to be compounded increases, likewise polyvinylpyrrolidone. Accordingly, polyvinylpyrrolidone and polyvinyl methyl ether are suitably used for the calcium hydroxide-based root canal filling material according to the invention. An amount of polyvinylpyrrolidone and/or polyvinyl methyl ether to be compounded must be 3 to 20% by weight. When the amount of polyvinylpyrrolidone and/or polyvinyl methyl ether to be compounded is less than 3% by weight, the viscosity-imparting effect is low. On the other hand, when the amount of polyvinylpyrrolidone and/or polyvinyl methyl ether to be compounded exceeds 20% by weight, the viscosity of the resulting paste increases, whereby the fluidity is liable to be rather lowered. The preparation of the calcium hydroxide-based root canal filling material according to the present invention is obtained by adding calcium hydroxide to a mixture of polyvinylpyrrolidone and/or polyvinyl methyl ether and water and well mixing to form a paste. An amount of calcium hydroxide to be compounded must be 30 to 60% by weight, at which the remedy effect is to exhibit sufficiently. In this regard, it is preferred from the standpoint of an improvement in the operability that the resulting paste is filled in a syringe cylinder or the like, which is then made in a wrapping state by capping its tip portion so as to be not dried.

In addition, the calcium hydroxide-based root canal filling material according to the present invention can be added with at least one X-ray opacity medium selected from barium sulfate, zirconium oxide, bismuth subnitrate, bismuth trioxide, and bismuth carbonate, for the purpose of enhancing the X-ray opacities; can be added with at least one disinfectant selected from iodoform and iodine, for the purpose of enhancing the disinfection properties; and can be added with both at least one of the above-described X-ray opacity media and at least one of the above-described disinfectants. Amounts of the X-ray opacity medium and the disinfectant are preferably 5 to 20 parts by weight and 0.5 to 5 parts by weight, respectively based on 100 parts by weight of the calcium hydroxide-based root canal filling material comprising 3 to 20%) by weight of polyvinylpyrrolidone and/or polyvinyl methyl ether, 30 to 60% by weight of calcium hydroxide, and 35 to 60% by weight of water. In the case of the X-ray opacity medium, the X-ray opacity effect tends to be hardly obtained effectively for less than 5 parts by weight and the disinfection effect by calcium hydroxide tends to be hardly obtained for its addition excess 20 parts by weight. Further, in the case of the disinfectant, the disinfection effect tends to be hardly obtained effectively for less than 0.5 parts by weight and the biodetrimental effect of the calcium hydroxide-based root canal filling material possibly increases for its addition excess 5 parts by weight.

The calcium hydroxide-based root canal filling material according to the present invention will be described with reference to the following Examples, but it should not be construed that the invention is limited thereto.

EXAMPLE 1

10% by weight of polyvinyl pyrrolidone was dissolved in 40% by weight of water, and 50% by weight of calcium hydroxide was added to the solution, followed by well mixing to form a paste. The thus obtained calcium hydroxide-based root canal filling material was charged into a syringe cylinder, and a 25-guage (inner diameter 0.26 mm) needle was set in a tip of the syringe cylinder. The case where the filling material could be easily extruded was evaluated to be good, whereas the case where the filling material could be hardly extruded was evaluated to be bad.

EXAMPLES 2 TO 10

Calcium hydroxide-based root canal filling material were prepared and evaluated in the same manner as in Example 1, except that the formula was changed as shown in Table 1. The results obtained are summarized and shown in Table 1.

TABLE 1

| | Polyvinyl-pyrrolidone (% by weight) | Polyvinyl methyl ether (% by weight) | Water (% by weight) | Calcium hydroxide (% by weight) | Barium sulfate (part by weight) (Note 1) | Bismuth subnitrate (part by weight) (Note 1) | Bismuth trioxide (part by weight) (Note 1) | Bismuth carbonate (part by weight) (Note 1) | Iodoform (part by weight) (Note 1) | Iodine (part by weight) (Note 1) | Operability from the standpoint of fluidity |
|---|---|---|---|---|---|---|---|---|---|---|---|
| Example 1 | 10 | | 40 | 50 | | | | | | | Good |
| Example 2 | 5 | | 37 | 58 | 8 | | | | | | Good |
| Example 3 | 17 | | 43 | 40 | | | 14 | | | | Good |
| Example 4 | | 5 | 40 | 55 | | 10 | | | | | Good |
| Example 5 | 5 | | 42 | 53 | | | | 6 | 1 | | Good |
| Example 6 | | 15 | 45 | 40 | | | | 8 | | 2 | Good |
| Example 7 | | 7 | 38 | 55 | 10 | | | | 3 | | Good |
| Example 8 | 7 | 7 | 35 | 51 | | | | | 2 | 2 | Good |
| Example 9 | 5 | 7 | 40 | 48 | 5 | 5 | | 3 | | | Good |
| Example 10 | 8 | 7 | 50 | 35 | 5 | | 5 | 3 | 2 | | Good |

(Note 1): Content based on 100 parts by weight of the calcium hydroxide-based root canal filling material comprising polyvinylpyrrolidone and/or polyvinyl methyl ether, calcium hydroxide and water Comparative Example 1

As a formula from which polyvinylpyrrolidone was eliminated, one consisting of 50% by weight of water and 50% by weight of calcium hydroxide was prepared and evaluated in the same manner as in Example 1. As a result, the operability from the stand point of fluidity was so bad that the formulation was hardly extruded from the 25-guage needle, and therefore, it was not proper for clinical use.

Comparative Example 2

A formula consisting of 10% by weight of propylene glycol in place of polyvinylpyrrolidone, 40% by weight of water and 50% by weight of calcium hydroxide was prepared and evaluated in the same manner as in Example 1. As a result, the operability from the standpoint of fluidity was so bad that the formula was hardly extruded from the 25-guage needle, and therefore, it was not proper for clinical use.

As described above, the calcium hydroxide-based root canal filling material according to the present invention has the following characteristics, and its clinical merits are therefore great.
(1) The bioaffinity is superior.
(2) 30 to 60% by weight of calcium hydroxide can be contained, and the disinfection properties as an original object of calcium hydroxide can be expected.
(3) The fluidity is superior, and the operability such that calcium hydroxide can be sufficiently fed into a complicated root canal can be revealed.

In the light of the above, when the calcium hydroxide-based root canal filling material according to the present invention is used, not only a dentist can use with confidence, but also a patient can expect to receive a safe and comfortable medical care. Consequently, the invention is greatly valuable in contribution to the dental remedy field.

While the present invention has been described in detail and with reference to specific embodiments thereof, it will be apparent to one skilled in the art that various changes and modifications can be made therein without departing from the spirit and scope thereof.

What is claimed is:

1. A calcium hydroxide-based root canal filling material comprising 3 to 20% by weight of polyvinylpyrrolidone and/or polyvinyl methyl ether, 30 to 60% by weight of calcium hydroxide, and 35 to 60% by weight of water.

2. The calcium hydroxide-based root canal filling material as claimed in claim 1, further comprising 5 to 20 parts by weight of at least one X-ray opacity medium selected from the group consisting of barium sulfate, zirconium oxide, bismuth subnitrate, bismuth trioxide, and bismuth carbonate based on 100 parts by weight of the calcium hydroxide-based root canal filling material.

3. The calcium hydroxide-based root canal filling material as claimed in claim 1, further comprising 0.5 to 5 parts by weight of at least one disinfectant selected from the group consisting of iodoform and iodine based on 100 parts by weight of the calcium hydroxide-based root canal filling material.

4. The calcium hydroxide-based root canal filling material as claimed in claim 1, further comprising 5 to 20 parts by weight of at least one X-ray opacity medium selected from the group consisting of barium sulfate, zirconium oxide, bismuth subnitrate, bismuth trioxide, and bismuth carbonate and 0.5 to 5 parts by weight of at least one disinfectant selected from iodoform and iodine based on 100 parts by weight of the calcium hydroxide-based root canal filling material.

5. A method of dispensing the calcium-based root canal filling of claim 1 comprising charging said calcium-based root canal filling into a syringe cylinder fitted with a needle, and extruding said calcium-based root canal filling.

6. A method for disinfecting a root canal comprising applying the calcium-based root canal filling of claim 1 within a root canal.

* * * * *